US012648941B2

(12) United States Patent
Lund et al.

(10) Patent No.: US 12,648,941 B2
(45) Date of Patent: Jun. 9, 2026

(54) PIPERIDINE UREA DERIVATIVES FOR USE AS INOTROPIC AGENTS

(71) Applicants: Helsinn Healthcare SA, Lugano/Pazzallo (CH); Anacardio AB, Solna (SE)

(72) Inventors: Lars Lund, Stockholm (SE); Alberto Bernareggi, Cernobbio (IT); Emanuela Lovati, Mendrisio (CH); Claudio Giuliano, Como (IT); Claudio Pietra, San Martino Siccomario (IT)

(73) Assignees: Helsinn Healthcare SA, Lugano/Pazzallo (CH); Anacardio AB, Solna (SE)

( * ) Notice: Subject to any disclaimer, the term of this patent is extended or adjusted under 35 U.S.C. 154(b) by 360 days.

(21) Appl. No.: 18/566,301

(22) PCT Filed: Jun. 2, 2022

(86) PCT No.: PCT/EP2022/065013
§ 371 (c)(1),
(2) Date: Dec. 1, 2023

(87) PCT Pub. No.: WO2022/253941
PCT Pub. Date: Dec. 8, 2022

(65) Prior Publication Data

US 2024/0277688 A1 Aug. 22, 2024
US 2025/0205216 A2 Jun. 26, 2025

(30) Foreign Application Priority Data

Jun. 2, 2021 (EP) ..................................... 21177292

(51) Int. Cl.
*A61K 31/4468* (2006.01)
*A61P 9/04* (2006.01)
*A61P 9/10* (2006.01)

(52) U.S. Cl.
CPC ............ *A61K 31/4468* (2013.01); *A61P 9/04* (2018.01); *A61P 9/10* (2018.01)

(58) Field of Classification Search
CPC .................................................. A61K 31/4468
See application file for complete search history.

(56) References Cited

FOREIGN PATENT DOCUMENTS

| | | |
|---|---|---|
| EP | 3542799 A1 | 9/2019 |
| WO | 2012116176 A2 | 8/2012 |
| WO | 2015134839 A1 | 9/2015 |

OTHER PUBLICATIONS

Nagaya et al., Circulation et al, (2004) pp. 3674*3679.*
Clinical Perspective, "Is sinus bradycardia a factor facilitating overt heart failure?," European Heart Journal (1999) 20, 252-255.
Nagaya et al. "Effects of Ghrelin Administration on Left Ventricular Function, Exercise Capacity, and Muscle Wasting in Patients With Chronic Heart Failure," Circulation 2004, 3674-3679.
Schwenke et al. "Early Ghrelin Treatment after Myocardial Infarction Prevents an Increase in Cardiac Sympathetic Tone and Reduces Mortality," Endocrinology 149(10):5172-5176, 2008.
National Center for Biotechnology Information. PubChem Compound Summary for HM01 (CID 146170991); Jun. 20, 2020; 22 pages.
International Search Report corresponding to International Patent Application No. PCT/EP2022/065013, mailed Sep. 29, 2022, 14 pages.
Qiang Sun, et al.: "Effects of GH secretagogues on contractility and Ca<2+> homeostasis of isolated adult rat ventricular myocytes", ENDOCRINOLOGY, vol. 151, No. 9, Sep. 1, 2010 (Sep. 1, 2010), pp. 4446-4454.

* cited by examiner

*Primary Examiner* — Paul Ward
(74) *Attorney, Agent, or Firm* — McNeill PLLC

(57) ABSTRACT

The invention concerns the use of compounds represented by formula (I)

(I)

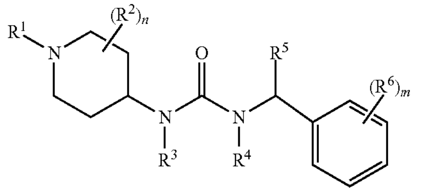

as inotropic agents. The compounds of formula (I), which include, as preferred, 1-[(1S)-1-(2,3-dichloro-4-methoxyphenyl)ethyl]-3-methyl-3-[(4R)-1-methyl-3,3-dimethyl-4-piperidyl]-urea and its hydrochloride salt, are herein reported to have a significant inotropic activity on cardiomyocytes from both normal and myocardial infarction-induced heart failure animal models, which makes them useful for treating cardiovascular patients in need thereof. Differently from known inotropic agents, the present compounds are effective on cardiomyocyte contractility without influencing calcium mobilization. Accordingly, they are advantageously free from adverse effects caused by increased calcium concentrations, such as increased oxygen demand, tachycardia, arrhythmia, ischemia, etc. Overall, a new, safe and effective inotropic treatment is thus made available.

18 Claims, 6 Drawing Sheets

PIPERIDINE UREA DERIVATIVES FOR USE AS INOTROPIC AGENTS

CROSS-REFERENCE TO RELATED APPLICATIONS

This application is a national phase entry pursuant to 35 U.S.C. § 371 of International Application No. PCT/EP2022/065013, filed Jun. 2, 2022, which claims priority to European Patent Application No. 21177292.6, filed Jun. 2, 2021, the entire contents of which are incorporated by reference in their entireties.

STATE OF THE ART

Heart failure (HF), also known as congestive heart failure, is a common, serious pathological condition characterized by an insufficient heart pumping capability, which fails to maintain the rate of blood flow needed for body metabolism, or can do so only secondary to neurohormonal activation, leading to, among other things, fluid retention and signs and symptoms of heart failure. HF is the leading cause of hospitalization amongst older adults. In 2015, it affected about 40 million people globally. Overall, around 2% of adults have heart failure and in those over the age of 65, this increases to 6-10%. HF may have fatal consequences, with a risk of death of about 35% in the first year after diagnosis.

Signs and symptoms of heart failure commonly include shortness of breath, excessive fatigue, and leg swelling. The shortness of breath usually worsens with exercise or while lying down and may wake the person at night. Common causes of heart failure include coronary artery disease, including a previous myocardial infarction (heart attack), high blood pressure, atrial fibrillation, valvular heart disease, excess alcohol use, infection, and cardiomyopathy of an unknown cause. These factors cause heart failure by changing the structure and/or the function of the heart. HF may be associated with reduced ejection fraction (HFrEF) or with preserved ejection fraction (HFpEF), depending on whether the physiological ability of the left ventricle to contract or relax is lost or preserved.

Treatment of HF depends on the severity and cause of the disease. In people with chronic stable heart failure regardless of ejection fraction, treatment commonly consists of lifestyle modifications such as stopping smoking, physical exercise, and dietary changes, treatment of underlying risk factors such as hypertension, and relief of symptoms with diuretics. The class of drugs useful for treating HF is intrinsically very diversified, comprising molecules with different effects and mechanisms of action, such as: vasodilators, aimed to expand blood vessels, ease blood flow and reduce blood pressure; diuretics and aldosterone antagonists, aimed to help with fluid retention; ACE inhibitors, ARB or ARNi drugs, aimed to improve heart function and life expectancy; *digitalis* glycosides aimed to strengthen the heart's contractions; anticoagulants or antiplatelets to prevent blood clots; beta-blockers to improve heart function; SGLT2-inhibitors which have complex beneficial effects, tranquilizers to reduce anxiety. For example, in patients with heart failure due to reduced ejection fraction, angiotensin converting enzyme inhibitors, angiotensin receptor blockers, or sacubitril/valsartan (ARNi), along with beta-blockers, mineralocorticoid receptor antagonists, and sodium-glucose co-transporter 2—inhibitors (SGLT2-inhibitors) are recommended.

The above approaches, aimed to block and potentially reverse the adverse structural and/or functional cardiac changes in HFrEF, also reduce the risk of hospitalization for heart failure and death. However, they fail to address the underlying pathology of HF:reduced heart contractility. Drugs that increase contractility (conventionally termed inotropes) are also available:they include phosphodiesterase-3 (PDE3)-inhibitors (e.g. milrinone) and adrenergic agonists (e.g. dobutamine). These agents generally work by increasing calcium concentrations, which causes a number of adverse effects, including increased myocardial oxygen demand, ischemia, arrhythmia and they also cause excessive hypotension through various mechanisms. Levosimendan is available in some countries and acts in part by increasing calcium sensitivity, but it also acts through PDE3-inhbition, increasing calcium concentrations and causing arrhythmias, and also acts on the vasculature, causing hypotension.

A new class of inotropes, myosin activators, are in development but there are concerns that they may induce ischemia and cause elevations in troponin, and phase 3 outcomes suggest no benefit on CV-mortality (New England Journal of Medicine 2021 Jan 14;384(2):105-116). Increased troponin levels have been reported in case of sepsis, kidney diseases, pulmonary embolism, heart infection and heart failure too, with significant prognostic value.

Ghrelin is a hormone produced by cells of the gastrointestinal tract, which stimulates the release of growth hormone, increases gastric motility/secretion, and stimulates appetite and food intake. Ghrelin also participates in regulation of reward cognition learning and memory, the sleep-wake cycle, taste sensation, reward behavior, and glucose metabolism. Cardiovascular effects are also reported for ghrelin: in healthy subjects, it dilates arteries, decreases blood pressure, reduces cardiac afterload and increases cardiac output (*Hypertension,* 2014, 64, 450-454). Regarding possible inotropic effects of ghrelin, conflicting reports are present in the literature. In *Endocrinology* 2010, 15(1), 4446-4454, heart perfusion of ghrelin after ischemia was found to produce an inotropic effect on cardiomyocytes. However, in Peptides, 2006, 27(7), 1616-1623, ghrelin was found to produce a negative inotropic effect, partly mediated by $K_{Ca}$ channels. The publication *International Journal of Cardiology,* 2009, 137(3), 267-275 reports no effects of human ghrelin on cardiac function in a rat model of heart failure; likewise, no inotropic effects were found for ghrelin in isolated paced atria (*Cardiovascular Research,* 2006, 69, 227-235).

Growth hormone secretagogues are synthetic peptides, which, similarly to ghrelin, stimulate the secretion of growth hormones. Some of them may display cardiovascular effects, such as increased coronary resistance, accelerated heart rate and cardiotropic effects, the latter being obtained via calcium mobilization (*Endocrinology,* 2003, 144(11), 5050-5057).

Families of asymmetric urea derivatives with ghrelin modulating activity are disclosed in WO2012/116176 and in WO2015/134839, for use in the treatment of ghrelin-mediated diseases; no experimental evidence is present in these documents of any cardiac effects for any of the disclosed compounds. The further application WO2019/179878 is focused on the hydrochloride salt of 3-(1-(2,3-dichloro-4-methoxyphenyl)ethyl)-1-methyl-(1,3,3-trimethylpiperidin-4-yl)urea, having enhanced brain permeation properties, and being used for treating a number of neurological disorders; the compound is also reported to have a centrally-mediated bradycardic effect; bradycardia is discussed by the literature as a possible factor which, if severe, can facilitate overt heart failure but if mild can be protective in heart failure (*European Heart Journal,* 1999, 20,252-255). The publication

*Endocrinology,* 2010, 151(9), pp. 4446-4454 reports calcium-mediated positive inotropic effects for the natural growth hormone secretagogues ghrelin (a 28-aminoacid polypeptide) and its analogue hexarelin; the article also acknowledges the existence of conflicting reports on the effects of the general class of growth hormone secretagogues, including reported cases of negative inotropic effects.

In view of the above prior art, the need remains high for medicaments capable to address the core issue and underlying cause of HF, i.e. the reduced heart contractility, which are safe and with no adverse effects, in particular those adverse effects caused by calcium mobilization.

SUMMARY OF THE INVENTION

The present inventors have unexpectedly found that the compounds represented by formula (I)

(I)

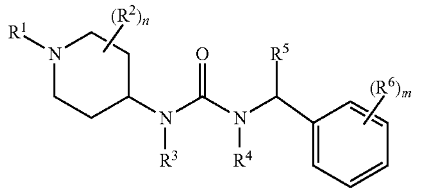

whose radicals $R^1$-$R^6$ and indexes m,n are defined in the detailed description, have a distinct inotropic activity on cardiomyocytes, which makes them useful for treating cardiovascular patients in need thereof.

The present compounds, which include, as preferred, 1-[(1S)-1-(2,3-dichloro-4-methoxyphenyl)ethyl]-3-methyl-3-[(4R)-1-methyl-3,3-dimethyl-4-piperidyl]-urea and its hydrochloride salt, are thus effective in the treatment of pathological conditions characterized or connected with a reduced and/or ineffective heart contractility.

Examples of these conditions are heart failure, heart attack, cardiogenic shock, septic shock, myocardial infarction, cardiomyopathy, pulmonary artery hypertension (PAH), etc. A preferred indication is heart failure, which can be any of type (i.e. acute or chronic and reduced or preserved ejection fraction), severity (mild, moderate or severe) and stage (i.e. initial or advanced). A more preferred indication is advanced heart failure, either acute or chronic. A most preferred indication is advanced heart failure, either acute or chronic, with reduced ejection fraction (HFrEF). A preferred example of cardiomyopathy is dilated cardiomyopathy (DCM), in particular, DCM due to genetic variants (also known as familial DCM). A preferred example of PAH is PAH with right ventricular systolic function.

The compounds of formula (I), including the compound 1-[(1S)-1-(2,3-dichloro-4-methoxyphenyl)ethyl]-3-methyl-3-[(4R)-1-methyl-3,3-dimethyl-4-piperidyl]-urea and its hydrochloride salt are further useful in that they exert inotropic activity without affecting calcium mobilization: in fact, rather than enhancing calcium concentrations in the cardiomyocyte cytosol, they act by enhancing cardiomyocyte sarcomere sensitivity to the existing calcium levels. Consequently, the present compounds obtain a significant inotropic response in patients in need thereof, while avoiding the common adverse effects of known inotropic agents caused by increased calcium concentrations in the cardiomyocyte cytosol, herein briefly referred as "increased calcium concentrations", such as increased oxygen demand, tachycardia, arrhythmia, ischemia, etc. Overall, a new, safe and effective inotropic treatment is thus made available.

DESCRIPTION OF THE FIGURES

FIG. 1 (bottom): AC01/HM01 induced an increase in contractility which was inhibited by D-Lys3 (a specific ghrelin antagonist), in cardiomyocytes isolated from hearts of both SHAM and heart failure (HF) mice (mice underwent ligation of the left anterior descending artery causing myocardial infarction; after several weeks, the mice developed heart failure): Cardiomyocyte contractility increased with the ghrelin receptor agonist AC01/HM01 (1 μM), while the pretreatment with the ghrelin receptor antagonist D-Lys3-GHRP-6 (3 μM) blocked the contractile effect. Cardiomyocytes isolated from both SHAM (left) and MI groups (right) positively responded to AC01/HM01 by increasing their contractility. (* $p<0.05$, ** $p<0.01$). Bar graph shows the average of N cells analyzed as stated.

FIG. 2 (bottom right): Bar graphs show average $Ca^{2+}$ transients of N cells analyzed as stated (p=not significant for all comparisons)).

(bottom): Bar graph showing expression levels of phospho-Tnl expressed as fold changes over vehicle treated cardiomyocytes. Batches of cardiomyocytes (~$10^5$ cells)

were collected in tubes and treated as stated. Bar graph shows the average of N batches analyzed as stated (* $p<0.05$,  $p<0.01$, * $p<0.001$), FIG. 5. Protein kinase A (PKA) activity in isolated cardiomyocytes. Cardiomyocytes treated with AC01/HM01 (1 μM) displayed a reduction of PKA activity (grey bar). D-Lys 3-GHRP-6 blocked the AC01/HM01 intracellular signaling and restored the PKA activity to physiologic levels (red bar), similar to cardiomyocytes treated with vehicle (white bar). Batches of cardiomyocytes (~$10^5$ cells) were collected in tubes and treated as stated. Bar graph shows the average of N batches.

Figure 6:
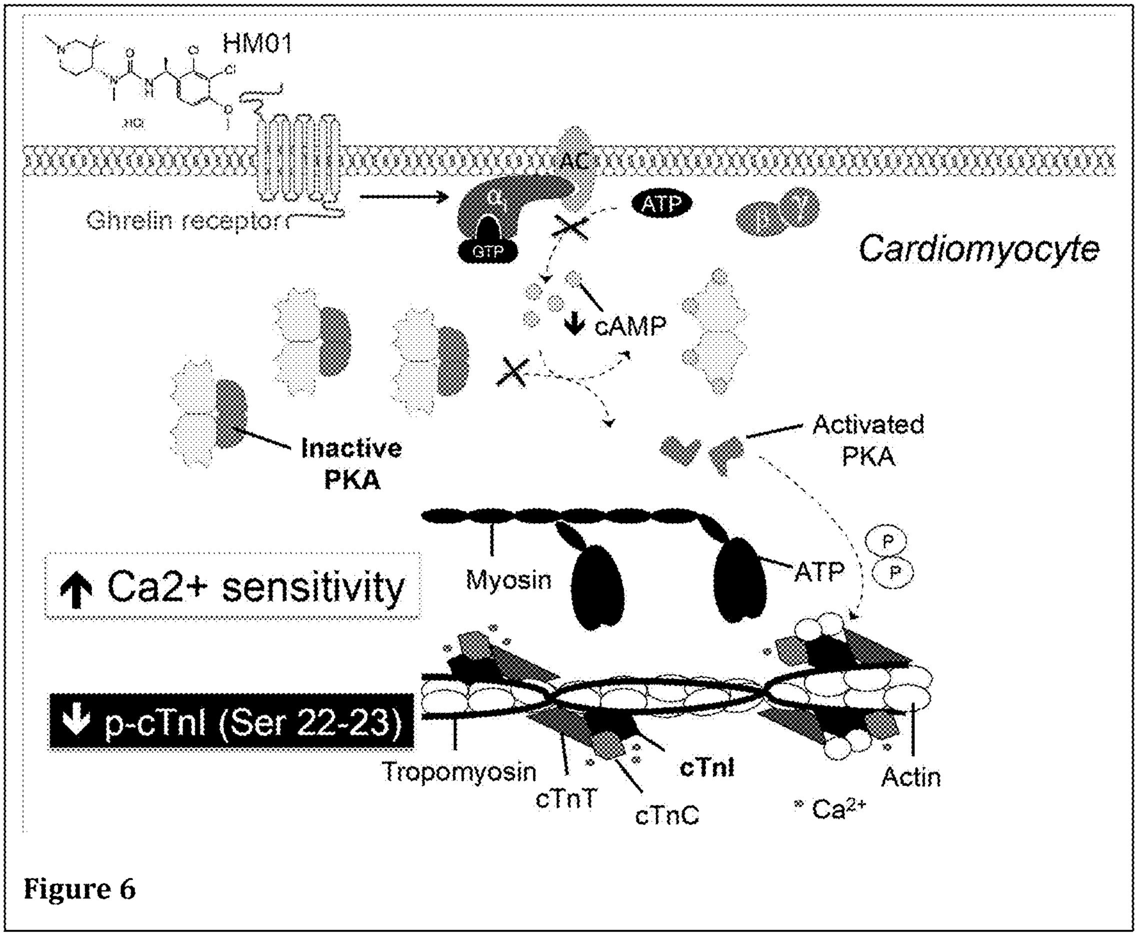

FIG. 6. Molecular signaling triggered by AC01/HM01 and Ghrelin receptor interaction: AC01/HM01 activates Gai signaling, which is linked to reduced activity of PKA and decreased phosphorylation of cTnl at Serine 22-23. This mechanism is responsible of the enhanced sensitivity to $Ca^{2+}$ in cardiomyocytes and improved contractility following AC01/HM01 stimulation.

DETAILED DESCRIPTION OF THE INVENTION

A first main object of the invention is the provision of a compound of formula (I) or a pharmaceutically acceptable salt thereof of formula (I) for use as inotropic agent.

(I)

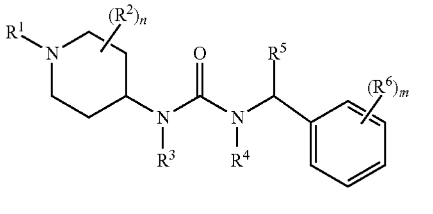

In the present formula (I):

$R^2$, $R^3$, $R^5$ independently from each other are $C_1$-$C_6$ alkyl, $R^1$, $R^4$, independently from each other are hydrogen or $C_1$-$C_6$ alkyl, $R^6$ is $C_1$-$C_6$ alkyl, halo, $C_1$-$C_6$ alkoxy or $C_1$-$C_6$ haloalkyl, n is 2-3 m is 1-3.

Overall in the present formula (I): the term "alkyl" includes both linear and branched alkyls; the terms "$C_1$-$C_n$" disclose each of the single homologs of the 1-n range, e.g. the term $C_1$-$C_6$ is equivalent to $C_1$, $C_2$, $C_3$, $C_4$, $C_5$, $C_6$.

In a general preferred embodiment, $R^4$ is hydrogen.

In a more preferred embodiment, $R^4$ is hydrogen and n is 2.

In an even more preferred embodiment, $R^4$ is hydrogen, n is 2 and $R^2$ is methyl.

In a further more preferred embodiment, $R^4$ is hydrogen, n is 2, $R^2$ is a methyl, and the two $R^2$ groups are attached to the same carbon atom of the piperidine ring, in particular a carbon atom which is not directly connected to the piperidine nitrogen atom, i.e. they are attached to the 3-yl position of the piperidine ring (being equivalent to the 5-yl position).

In preferred variants, all the above presented embodiments may be further characterized by one or more, preferably all, of the following conditions:

both $R^3$, and $R^5$ are $C_1$-$C_3$ alkyl, preferably methyl.

m is 3

$R^6$ is halo and/or alkoxy, preferably with at least one $R^6$ being alkoxy.

The compounds of formula (I) in which $R^1$ is $C_1$-$C_6$ alkyl represent a generally applicable variant; alternatively, the compounds of formula (I) in which $R^1$ is hydrogen represent another generally applicable variant.

The term "halo" indicates herein chlorine, fluorine, bromine or iodine; preferably the term "halo" indicates chlorine; preferably, the term alkoxy indicates methoxy or ethoxy.

The term "pharmaceutically acceptable salt" means herein any salt which is usually deemed as non-toxic in pharmaceutical practice; in particular, being the compounds of formula (I) salt-forming amines, any suitable salt-forming acid can be used in pharmaceutical practice to form a pharmaceutically acceptable salt from the free base of formula (I); a typical pharmaceutically acceptable salt is the hydrochloric acid salt (hydrochloride), in particular the monohydrochloride.

The compounds of formula (I) contain two asymmetric carbon atoms and can exist in different stereoisomeric forms and mixtures thereof, all being comprised by present formula (I); among them, preferred is the form 1(S), 4(R), which corresponds to the structure:

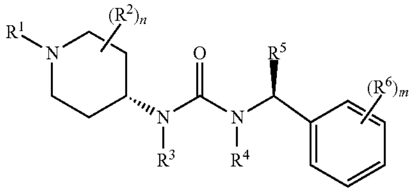

wherein $R^1$, $R^2$, $R^3$, $R^4$, $R^5$, $R^6$, m and n have the meanings defined above. In a particularly preferred embodiment, the compound of formula (1) is 1-[(1S)-1-(2,3-dichloro-4-methoxyphenyl)ethyl]-3-methyl-3-[(4R)-1-methyl-3,3-dimethyl-4-piperidyl]-urea, or a pharmaceutically acceptable salt thereof, in particular the monohydrochloride salt, having the following structure (Ia):

(Ia)

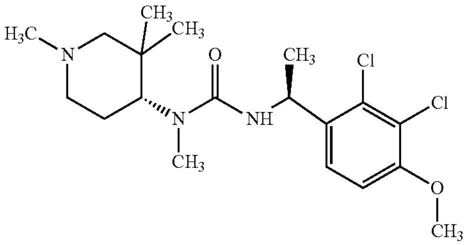

•HCl

The compound of structure (Ia) is known per se from e.g. Frontiers in Pharmacology, 2018, Vol. 9, article 869, pp. 1-16 and is herein referred for short as AC01 or HM01, indifferently.

The terms "inotropic agent", as well as the terms "inotropic activity" or "inotropic effect" when referred to the activity of the compounds of present formula (I), indicate that the compound in question is able to stimulate, i.e. enhance, the contractility and force of the patient's heart. The term inotropic means herein "positive" inotropic activity, i.e. the effect on the muscle is a stimulating one, and does not extend to opposite negative inotropic effect. The inotropic activity of the present compounds is effective on the heart muscle cells, i.e. myocardial cells, which translates into an enhanced contractility of the concerned muscular organ, i.e. the heart. The increased contractility improves heart functionality, in particular its strength of contraction, resulting in an enhanced pumping capability with consequent improved blood delivery and oxygenation of the various body districts.

Differently from available inotropic agents, the inotropic effect of the present compounds of formula (I) is not mediated by an increase of calcium concentrations; this effect is experimentally elicited by the evidence of no increase of calcium concentrations in the cardiomyocyte cytosol, i.e. no release and flux of calcium from the extracellular space and sarcoplasmic reticulum. It was thus unexpectedly found that these compounds are contractively effective without increasing the basal calcium concentrations of the muscular cell, i.e. they rather enhance the cellular sensitivity to the existing levels of calcium. The term "inotropic agent" can therefore be more precisely defined as "calcium sensitization-based" inotropic agent or, alternatively, as "calcium levels neutral" inotropic agent. The corresponding inotropic activity, typical of the present compounds of formula (I), is thus advantageously different from that of available inotropic agents in that it does not include the side effects due to increased cell calcium concentration, such as increased myocardial oxygen demand, ischemia, arrhythmia and excessive hypotension, etc. The medical use in question is thus further characterized as being free of the above-mentioned side effects linked to increased cell calcium concentration.

The present compounds of formula (I) are effective for use in the treatment of any pathological conditions of the human or animal patient characterized or connected with a reduced and/or ineffective heart contractility. Examples of these conditions are heart failure (also identified as congestive heart failure), heart attack, cardiogenic shock, septic shock, myocardial infarction, cardiomyopathy, pulmonary artery hypertension (PAH), etc. A preferred indication is heart failure: it may be any of type (i.e. acute or chronic; with reduced or preserved ejection fraction), severity (mild, moderate or severe) and stage (i.e. initial or advanced). A heart failure condition on which the present treatment is particularly needed/effective is heart failure with reduced ejection fraction (HFrEF), in particular advanced HFrEF, said heart failure being either acute or chronic. A particularly indicated treatment is chronic HFrEF, either in initial or advanced stage. A preferred example of cardiomyopathy is dilated cardiomyopathy (DCM), in particular, DCM due to genetic variants (also known as familial DCM). A preferred example of PAH is PAH with right ventricular systolic function.

The use according to the invention is particularly advantageous in conditions which require a long-lasting treatment with inotropic agents, such as the chronic forms of heart failure: in all these cases, avoiding the concomitant development of calcium-related side effects is particularly beneficial to the patient in that it prevents a prolonged exposition to dangerous consequences, which could be lethal in the long term, thus making available a safer inotropic therapy with a longer survival perspective.

Therefore, in a preferred embodiment, the present medical use is advantageously directed to a sub-population of patients for which the side effects linked to increased calcium concentration in the cardiomyocytes are especially to be avoided, i.e. patients who had, have or are at risk to have ischemia, arrhythmia and/or hypotension, which corresponds to a sub-group of more fragile cardiovascular patients, for which the arising of the above referred side-effects may be highly dangerous and possibly lethal.

The heart failure treated herein can be caused by any diseases that weaken the heart muscle, or diseases that cause stiffening of the heart muscles, or diseases that increase oxygen demand by the body tissue beyond the capability of the heart to deliver. Many diseases can impair the pumping action of the heart ventricles. For example, the muscles of the ventricles can be weakened by previous heart attacks or inflammation (myocarditis), leading over time to progressive heart failure. The diminished pumping ability of the ventricles due to muscle weakening is called systolic dysfunction. After each ventricular contraction, (systole) the ventricle muscles need to relax to allow blood from the atria to fill the ventricles. This relaxation of the ventricles is called diastole. Diseases such as hemochromatosis or amyloidosis can cause stiffening of the heart muscle and impair the ventricles' capacity to relax and fill; this is referred to as diastolic dysfunction. The most common cause of this is longstanding high blood pressure resulting in a thickened (hypertrophied) heart. Additionally, in some patients, although the pumping action and filling capacity of the heart may be normal, abnormally high oxygen demand by the body's tissues (for example, with hyperthyroidism) may make it difficult for the heart to supply an adequate blood flow (called high output heart failure). In some patients one or more of these factors can be present to cause congestive heart failure. Congestive heart failure can affect many organs of the body. For example, the weakened heart muscles may not be able to supply enough blood to the kidneys, which then begin to lose their normal ability to excrete salt (sodium) and water. This diminished kidney function can cause to body to retain more fluid. The lungs may become congested with fluid (pulmonary edema) and the person's ability to exercise is decreased. Fluid may likewise accumulate in the liver, thereby impairing its ability to rid the body of toxins and produce essential proteins. The intestines may become less efficient in absorbing nutrients and medicines. Over time, untreated or even if optimally treated with existing treatments, worsening congestive heart failure will affect virtually every organ in the body. This happens regardless of the original event that led to subsequent development of heart failure. The present treatment is thus further directed to treating all of the above mentioned symptoms and effects of heart failure.

The invention can be further characterized as the use of a compound of formula (I) or a pharmaceutically acceptable salt thereof as defined above in the manufacturing of an inotropic medicament for the treatment of any of the above pathological conditions. The invention is further characterized as a method of treating any of the above mentioned pathological conditions comprising administering a compound of formula (I) or a pharmaceutically acceptable salt thereof to a subject in need thereof.

Suitable subjects to whom the present treatment is addressed include mammalian subjects. Mammals include human subjects of either gender and at any stage of development; mammals further include but are not limited to, canine, feline, bovine, caprine, equine, ovine, porcine, rodents, lagomorphs, primates, and the like, and encompass mammals in utero.

Useful dose ranges may preferably range from 0.1 to 10 mg/day, e.g. 0.2 to 10 mg/day; the daily dose may be split in more than one daily administrations, preferably two daily administrations, e.g. 0.1 to 5 mg BID (twice daily).

The present compounds of formula (I) can be formulated in pharmaceutically administrable dosage forms suitable for administering the above referred daily doses. For example, they may contain the compound of formula (I) in amounts ranging from 0.1 to 10 mg, or a fraction of this amount, if intended for repeated daily administrations.

One of ordinary skill in the art will be able, without undue experimentation and in reliance upon personal knowledge and the disclosure of this application, to optimize these ranges in respect of the particular pharmaceutical form to be produced.

Solid dose form for oral administration can be, for example, presented in discrete units, such as hard or soft capsules, pills, cachets, lozenges, sachets, tablets or minitablets, each containing a predetermined amount of at least one of the disclosed compound. In some forms, the oral administration can be in a powder or granule form. In some forms, the oral dose form is sublingual, such as, for example, a lozenge or an oral film. In such solid dosage forms, the compounds of Formula I are ordinarily combined with one or more adjuvants. Such capsules or tablets can be controlled-release formulations. In the case of capsules, tablets, minitablets and pills, the dosage forms also can comprise buffering agents or can be prepared with enteric coatings.

Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

In some forms, the disclosed compositions can comprise a parenteral dose form. "Parenteral administration" includes, for example, subcutaneous injections, intravenous injections, intraperitoneally, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Typically, an appropriate amount of a pharmaceutically acceptable carrier is used in the formulation to render the formulation isotonic. Examples of the pharmaceutically acceptable carrier include, but are not limited to, saline, Ringer's solution and dextrose solution. Other acceptable excipients include, but are not limited to, thickeners, diluents, buffers, preservatives, surface active agents and the like.

The disclosed compounds can be administered by any suitable route, preferably in the form of a pharmaceutical composition adapted to such a route, and in a dose effective for the treatment or prevention intended. The active compounds and compositions, for example, can be administered orally, rectally, parenterally, ocularly, inhalationally, or topically. In particular, administration can be epicutaneous, inhalational, enema, conjunctival, eye drops, ear drops, alveolar, nasal, intranasal, vaginal, intravaginal, transvaginal, ocular, intraocular, transocular, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc. A preferred administration route is oral or intravenous.

The present compounds of formula (I) are generally administered at therapeutically effective amounts. A therapeutically effective amount may vary widely depending on the severity of the disease, the age and relative health of the subject, the potency of the compound used and other factors. Therapeutically effective amounts of compounds of Formula (I) may range from approximately 0.001 mg/Kg body weight to approximately 0.1 mg/Kg body weight, preferably from approximately 0.001 mg/Kg body weight to approximately 0.01 mg/Kg body weight. One of ordinary skill in the art will be able, without undue experimentation and in reliance upon personal knowledge and the disclosure of this application, to optimize these ranges in respect of each of the various pathological conditions mentioned above.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

As used in the specification and the appended claims, the singular forms "a," "an" and "the" include plural referents unless the context clearly dictates otherwise. Thus, for example, reference to the treatment of "a pathological condition" includes the treatment of two or more such conditions, even when occurring simultaneously in the same subject.

The word "or" or like terms as used herein means any one member of a particular list and also includes any combination of members of that list. "Optional" or "optionally" means that the subsequently described event or circumstance may or may not occur, and that the description includes instances where said event or circumstance occurs and instances where it does not.

The term "approximately," when used to modify the value of any parameter and ranges thereof, refers to experimental variations in the numerical quantity that can occur, for example, through typical measuring and handling procedures used for making compounds, compositions, etc.; through inadvertent error in these procedures; through differences in the manufacture, source, or purity of starting materials or ingredients used to carry out the methods; and like considerations. The term "approximately" also encompasses amounts that differ due to aging of a composition or formulation with a particular initial concentration or mixture, and amounts that differ due to mixing or processing a composition or formulation with a particular initial concentration or mixture. All these experimental variations are usually maintained within ±5% of the given value. Whether modified by the term "approximately" the claims appended hereto include equivalents to these quantities.

The term "comprise" and variations of the word, such as "comprising" and "comprises," means "including but not limited to," and is not intended to exclude, for example, other additives, components, integers or steps.

The term "treating" or "treatment" means the medical management of a patient with the intent to cure, ameliorate, stabilize, or prevent a disease, pathological condition, or disorder. These terms include active treatment, that is, treatment directed specifically toward the improvement from a disease, pathological condition, or disorder, and also includes causal treatment, that is, treatment directed toward removal of the cause of the associated disease, pathological condition, or disorder, with restoration of the original parameters of the patient prior to the disease, including increasing any parameter which had been pathologically reduced, such as heart contractility. These terms can mean that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease. In addition, these terms include palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. These terms mean both treatment having a curing or alleviating purpose and treatment having a preventive purpose. The treatment can be made either acutely or chronically. It is understood that treatment can mean a reduction or one or more symptoms or characteristics by at least 5% 10%, 20%, 30%, 40%, 50%, 60%, 70%, 80%, 90%, 95%, 99%, 99.9%, 99.99%, 100%, relative to a control. In the context of these terms, preventing refers to the ability of a compound or composition (such as the disclosed compounds and compositions) to prevent a disease identified herein in patients diagnosed as having the disease or who are at risk of developing such disease. In this context, preventing includes the delaying the onset of the disease relative to a control.

These terms do not require that the treatment in fact be effective to produce any of the intended results. It is enough that the results are intended.

Abbreviations, which are well known to one of ordinary skill in the art, may be used herein (e.g., “h” or “hr” for hour or hours, “g” or “gm” for gram(s), “mL” for milliliters, and “rt” for room temperature, “nm” for nanometers, “M” for molar, and like abbreviations).

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. and. If not mentioned, temperature is ambient temperature, and pressure is at or near atmospheric pressure.

EXPERIMENTALS

Example 1

Effect of HMO1 on Cardiomyocytes from a Mouse Model of Myocardial Infarction-Induced Heart Failure and from Control Mice Methods Ethical Approval for Animal Study Studies were performed at Karolinska Institutet, Stockholm, Sweden. The study was approved by the Stockholm North Ethical Committee on Animal Experiments. Animal experiments complied with the Swedish Animal Welfare Act, the Swedish Welfare ordinance, and recommendations and applicable regulations from Swedish authorities (Ethical permit 2155-2020 and N273-15). Animal experiments conformed to the guidelines from Directive 2010/63/EU of the European Parliament on the protection of animals used for scientific purposes. Mice were maintained on a 12-hour light/dark cycle and provided with food and water ad libitum.

Mouse Model of Myocardial Infarction-Induced Heart Failure

C57BL/6 mice, 12-16 weeks old, were anesthetized with a gas mixture of oxygen and isoflurane. Myocardial infarction (MI) was induced by permanent ligation of the left coronary artery, as previously described. SHAM-operated animals received the same procedure without coronary artery ligation (SHAM). The animals were terminated 4 weeks post procedure, when signs of heart failure (HF) were evident in the MI group: echocardiography showing reduced left ventricular fractional shortening (FS) and a non-contractile infarcted anterior wall (% FS M1=29.3±1.1, SHAM=61.4±2.1). After sedation, mice were euthanized through cervical dislocation and the hearts were collected and processed for cardiomyocyte isolation. The heart weight to body weight ratio was used as a parameter to assess cardiac hypertrophy (heart weight/body weight MI=9.5±1.3, SHAM=6.0±0.4). Moreover the heart of mice with MI revealed a necrotic infarcted area on the anterior LV wall, below the coronary occlusion, covering approximately ⅓ of the left ventricle. In total, 5 SHAM and 3 MI mice were used for the study.

Cardiomyocyte Isolation

Cardiomyocytes were isolated freshly from cardiac ventricles separately from SHAM and HF mice following the protocol developed by the Alliance for Cellular Signalling (AfCS Procedure Protocol ID PP00000125). From each of the 5 SHAM and 3 HF hearts a cell suspension was made and divided into 10 aliquots each, for a total of 50 aliquots from SHAM and 30 aliquots from HF hearts. These aliquots were treated with vehicle, AC01/HM01 or D-Lys3-GHPR-6+AC01/HM01 as stated and used for the subsequent physiological and biochemical experiments.

Reagents

AC01/HM01 was suspended in phosphate buffer saline solution (PBS: in mM: NaCl 137, KCl 7, $Na_2HPO_4$ 10, KH2PO4 1.8 M) and diluted to obtain 3 different concentrations: 0.2, 0.5 or 1 μM in Tyrode solution. We used a concentration range within 0.2-1 μM to ensure that the receptor was activated. D-Lys 3 GHRP-6 (ghrelin receptor antagonist; Sigma Aldrich, Stockholm, Sweden; $IC_{50}$ for antagonistic activity=0.9 μM) was suspended in PBS and used at 3 μM as final concentration in Tyrode solution (in mM: NaCl 121, KCl 5.0, CaCl2) 1.8, MgCl2 0.5, NaH2PO4 0.4, NaHCO3 24, EDTA 0.1, glucose 5.5). Prior to contractility and $Ca^{2+}$ signaling measurements and biochemical assays, cardiomyocyte suspensions from SHAM and HF hearts were randomized to 3 types of treatments: vehicle, AC01/HM01, or D-Lys3-GHPR-6+AC01/HM01. The treatment with different agents occurred for 15 minutes at room temperature. Some cell suspension aliquots were flash frozen in liquid N2 and stored at −80° C. for later biochemistry analyses. All the experiments were conducted blinded regarding the treatment of cardiomyocytes.

Confocal Imaging

Fresh isolated cardiomyocytes were aliquoted in 1.5 ml tubes and incubated with a cell permeable form of fluorescent Ca2+ indicator Fluo-3 AM followed by washing for >5 min. Before stimulation with different reagents the cells were plated on laminin coated glass bottom dishes (Mattek, Ashland, MA, USA), which compose a custom built perfusion/stimulation chamber, and continuously perfused with O2/CO2 (95/5%) bubbled Tyrode solution with the following composition (in mM: NaCl 121, KCl 5.0, CaCl2) 1.8, MgCl2 0.5, NaH2PO4 0.4, $NaHCO_3$24, EDTA 0.1, glucose 5.5), which represents the vehicle solution. 15 batches from SHAM and 9 batches from HF of cardiomyocytes were randomized to different treatments: vehicle, AC01/HM01 (0.2, 0.5 or 1 μM) or pretreatment with D-Lys3-GHPR-6 (3 μM) followed by AC01/HM01 (1 μM). The cardiomyocytes were stimulated at 1 Hz at supra-threshold voltage to contract using an electrical field between two platinum electrodes attached to the perfusion/stimulation chamber. Line scan fluorescence images were acquired using a confocal microscope (Biorad; 40× oil immersion lenses) only on cardiomyocytes that contracted upon electrical stimulation and displayed normal morphology (e.g. striated, "brick shaped"). Cells that displayed spontaneous contractions were not analyzed. ImageJ software (open source software developed by NIH, Bethesda, USA) was used to quantify changes in fluorescence (Ca2+ transients) and contractility of single cardiomyocytes.

Measurement of Cardiomyocyte Contractility

Fresh isolated cardiomyocytes were aliquoted in 1.5 mL tubes and incubated with a cell permeable form of the fluorescent $Ca^{2+}$ indicator Fluo-3 AM for approximately 20 minutes followed by washing for >5 min. The cells were plated on laminin coated glass bottom dishes (35 mm, Mattek, Ashland, MA, USA), and then mounted in a custom built perfusion/stimulation chamber. Cells were continuously perfused with O2/CO2 (95/5%) bubbled Tyrode solution with the following composition (in mM): NaCl 121, KCl 5.0, CaCl2 1.8, MgCl2 0.5, NaH2PO4 0.4, NaHCO3 24, EDTA 0.1, glucose 5.5, which represents the vehicle solution.

15 aliquots of cardiomyocyte suspension from SHAM and 9 aliquots from HF were randomized to different treatments: vehicle, AC01/HM01 (0.2, 0.5 or 1 μM) or pretreatment with D-Lys3-GHPR-6 (3 μM) followed by AC01/HM01 (1 μM). The cardiomyocytes were electrically stimulated to contract at 1 Hz with supra-threshold voltage using two platinum electrodes attached to the perfusion/stimulation chamber.

Line scan fluorescence images were acquired using a confocal microscope (Biorad; 40× oil immersion lenses). Images were recorded only from cardiomyocytes that contracted upon electrical stimulation and displayed normal morphology (e.g. striated, "brick shaped"). Cells that displayed spontaneous contractions were not analysed. ImageJ software (open source software developed by NIH, Bethesda, USA) was used to quantify changes in fluorescence ($Ca^{2+}$ transients) and contractility of single cardiomyocytes.

Measurement of Intracellular $Ca^{2+}$ $Ca^{2+}$ transients were measured using a confocal microscope (Biorad) in line scan mode. A wavelength of 491 nm was used for excitation and emitted light was collected at wavelength>515 nm. The line scan was oriented along the long axis of the cardiomyocyte. The fluorescent signal (F/Fo) was calculated as the ratio between resting fluorescence before the start of the $Ca^{2+}$ transient (FO) and the peak fluorescence (F) of the $Ca^{2+}$ transient.

Measurement of Cardiomyocyte Contractility

The contractility of cardiomyocytes was measured as the percent of length shortening (fractional shortening; % FS). Isolated cardiomyocytes were exposed in the perfusion chamber to the reagents above: vehicle or AC0/HM01 (0.2, 0.5 or 1 μM in Tyrode solution), with and without the Ghrelin receptor antagonist D-Lys3-GHPR-6 (3 μM in Tyrode solution).

Protein Immunoblotting

Aliquots of frozen cardiomyocyte suspensions were lysed using NP40 buffer (Thermo Fisher FNN0021, Stockholm, Sweden) supplemented with phosphatase inhibitors (Sigma-Aldrich P2850-1ML, P5726-1ML, Stockholm, Sweden). Protein lysates were separated by electrophoresis and transferred onto membranes. Membranes were incubated with primary antibody: rabbit anti phospho (Ser 22-23) cardiac troponin I (cTnl, Cell Signalling, Leiden, The Netherlands #4004S) and rabbit anti-cTnl (Cell Signalling #4002S, Leiden, The Netherlands). Thereafter, infrared-labelled secondary antibodies (IRDye 680 and IRDye 800, 1:5000, Licor) were used. Immunoreactive bands were analyzed using the Odyssey Infrared Imaging System (Li-Cor, Bad Homburg, Germany). Band densities were quantified with Image J (NIH, Bethesda, USA), normalized to total cTnl and final data was expressed as fold increase compared to bands representing protein extracted from vehicle treated cells.

PKA Activity Assay in Cardiomyocytes

Elisa-based PKA kinase activity assay kit (ab139435, Abcam, Cambridge, UK) was employed to determine PKA activity in cardiomyocytes. Aliquots of frozen cardiomyocytes were thawed and mixed with a lysis buffer containing (mM) the following: 20 MOPS, 50 β-glycerolphosphate, 5 EGTA, 2 EDTA, 1 benzamidine, 1 sodium orthovanadate, 1% NP40, 1 DTT, complete protease inhibitor cocktail (Roche Diagnostics, West Sussex, UK) and phosphatase inhibitor cocktail 3 (Sigma, Gillingham, UK). Approximately 2 μg of protein of each sample were assayed according to the manufacturer's instructions 27.

Statistics

Statistical comparison between 2 groups were performed using students t-test (unpaired). For comparison between >2 groups, ANOVA analysis was used. A $p<0.05$ was considered of statistical significance. Average data was presented as mean±standard error of the mean (SEM). In the figures, P values are indicated as follows: * $P<0.05$,  $P<0.01$, * $P<0.001$.

Results

Figure 1:
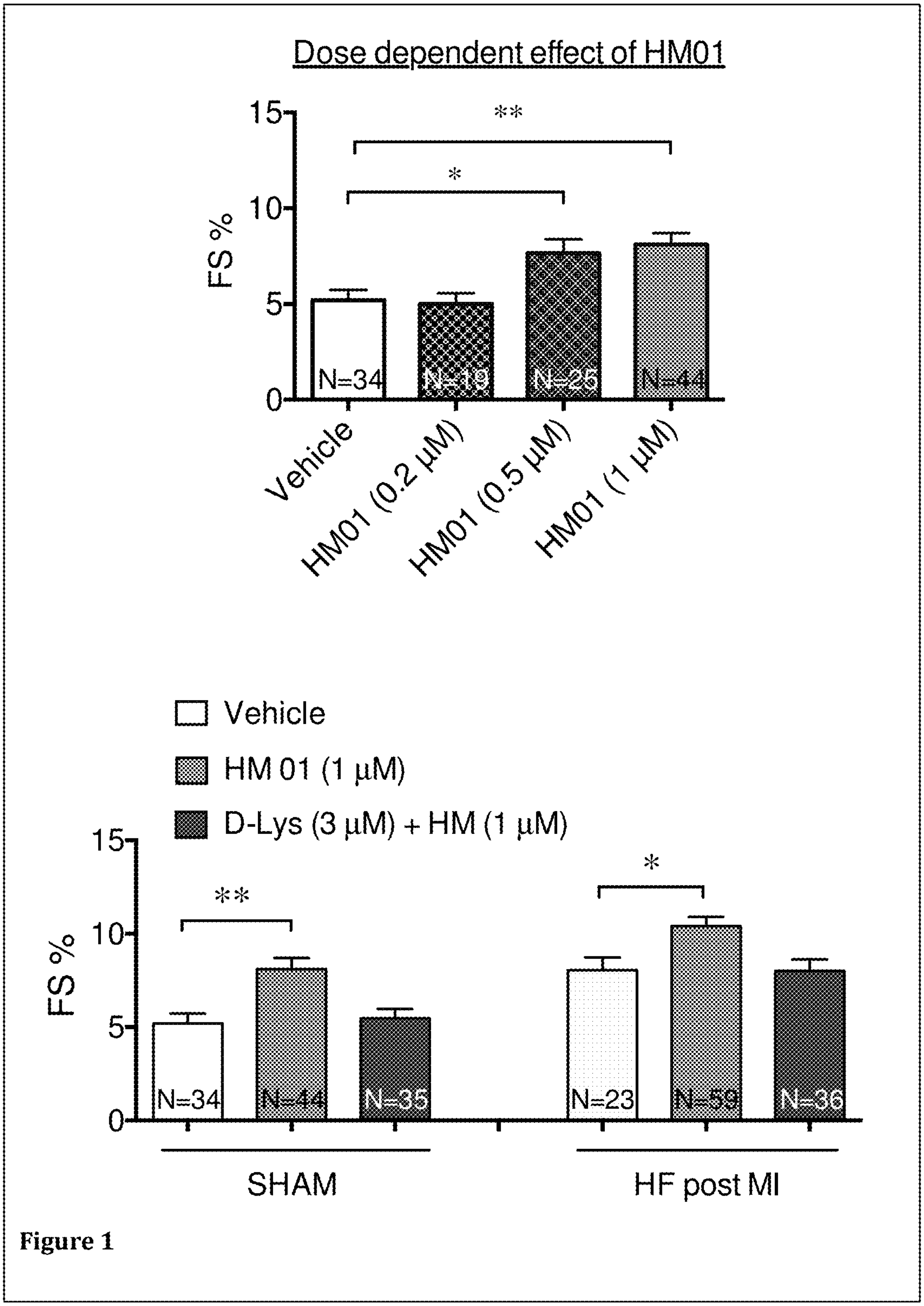
FIG. 1 (top): AC01/HM01 induced a dose-dependent increase contractility in mouse cardiomyocytes (top panel): The contractile effect of AC01/HM01 was measured in cardiomyocytes (SHAM, i.e. cardiomyocytes who underwent a sham procedure without inducing myocardial infarction) at different concentrations (0.2, 0.5 and 1 μM) using the changes in length fractional shortening (FS %) as readout. AC01/HM01 at 1 μM showed the greatest contractile effect compared to vehicle (* $p<0.05$, ** $p<0.01$). Bar graph shows the average fractional shortening of N cells analyzed as stated.

AC01/HMO1 Increased Cardiomyocyte Contractility (FIG. 1)

Contractility was measured in isolated cardiomyocytes in response to AC01/HM01 at different concentrations (0.2, 0.5 and 1 μM) vs. vehicle. FIG. 1 top shows that the contractility of SHAM cardiomyocytes, measured as percent of length fractional shortening (FS %), was increased in a dose-dependent manner with a considerable and statistically significant response at 0.5 and 1 μM of AC01/HM01. FIG. 1 bottom shows that cardiomyocytes treated with AC01/HM01 (1 μM) displayed a significant increase of contractility expressed as % of fractional shortening (FS %) compared to vehicle in both SHAM and HF, and that pretreatment with Ghrelin receptor antagonist, D-Lys 3 GHRP-6 (3 μM), blocked the contractile effect of AC01/HM01, suggesting that the molecular mechanism is specific for ghrelin receptor signalling. We used cardiomyocytes isolated from both control (SHAM) and myocardial infarction induced heart failure (HF) mice to measure contractility. Unrelated to treatment with AC01/HM01, cardiomyocyte contractility appeared to be higher in HF cardiomyocytes compared to SHAM. Viable cardiomyocytes from MI-induced HF, derived from the non-ischemic portion of the heart, compensate for the infarcted/necrotic myocardium by improving their contractility through enhancement of Ca2+ cycling and myofilament sensitivity. However, the increase in contractility induced by AC01/HM01 compared to vehicle treated cardiomyocytes was observed in both SHAM and HF, suggesting that this molecule can further improve contractility regardless of the state of cardiomyocytes.

Figure 2:
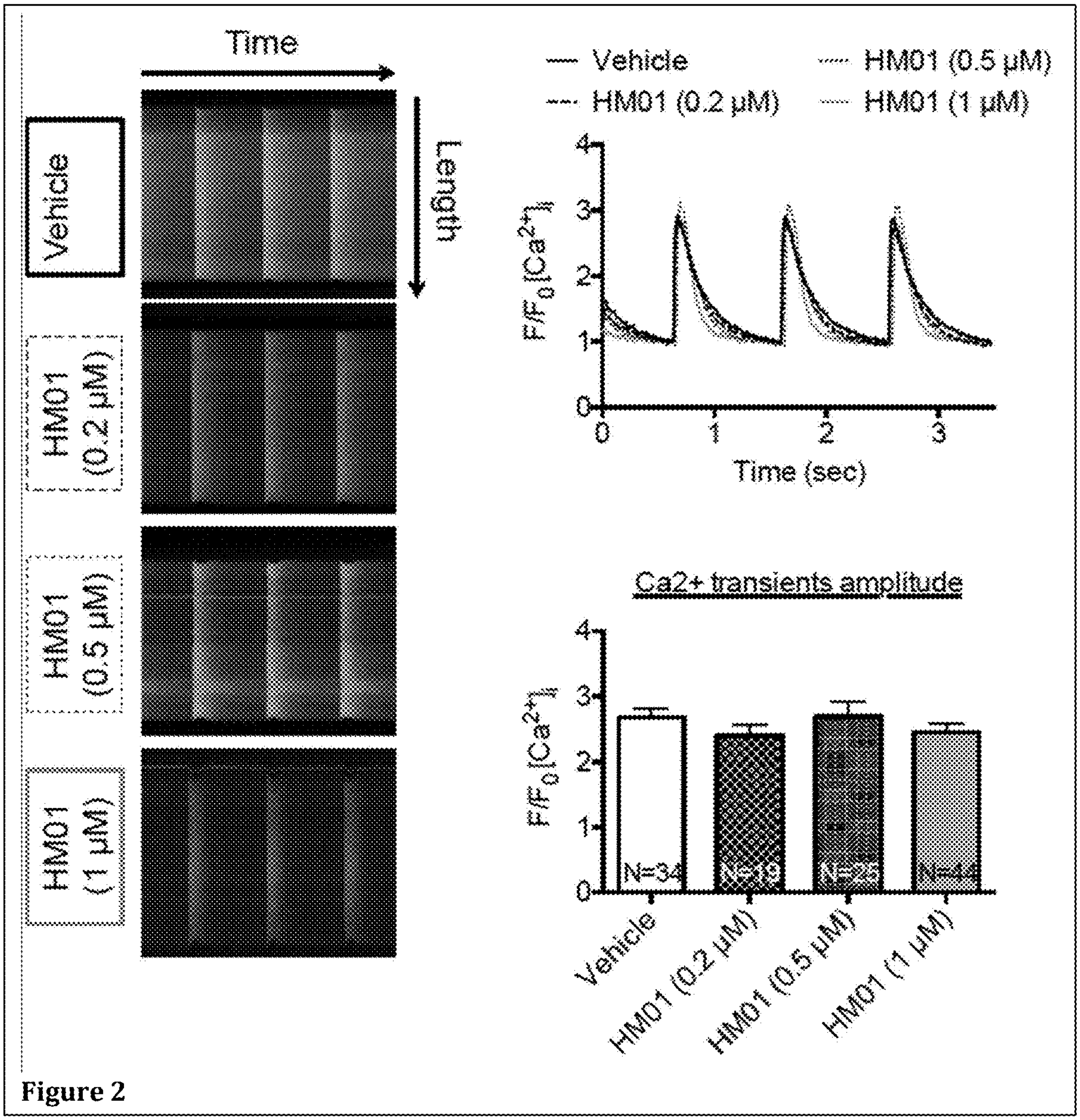
FIG. 2 (left and top right): Representative line scan image (left) and $Ca^{2+}$ transient (mobilization) curves (top right) in cardiomyocytes isolated from hearts of SHAM treated with vehicle or different concentrations of AC01/HM01. Treatment with AC01/HM01 did not cause alteration of $Ca^{2+}$ transient amplitudes at any concentrations, which show that the increased contractility in FIG. 1 is due to increased $Ca^{2+}$ sensitivity rather than $Ca^{2+}$ transients.
Figure 3:
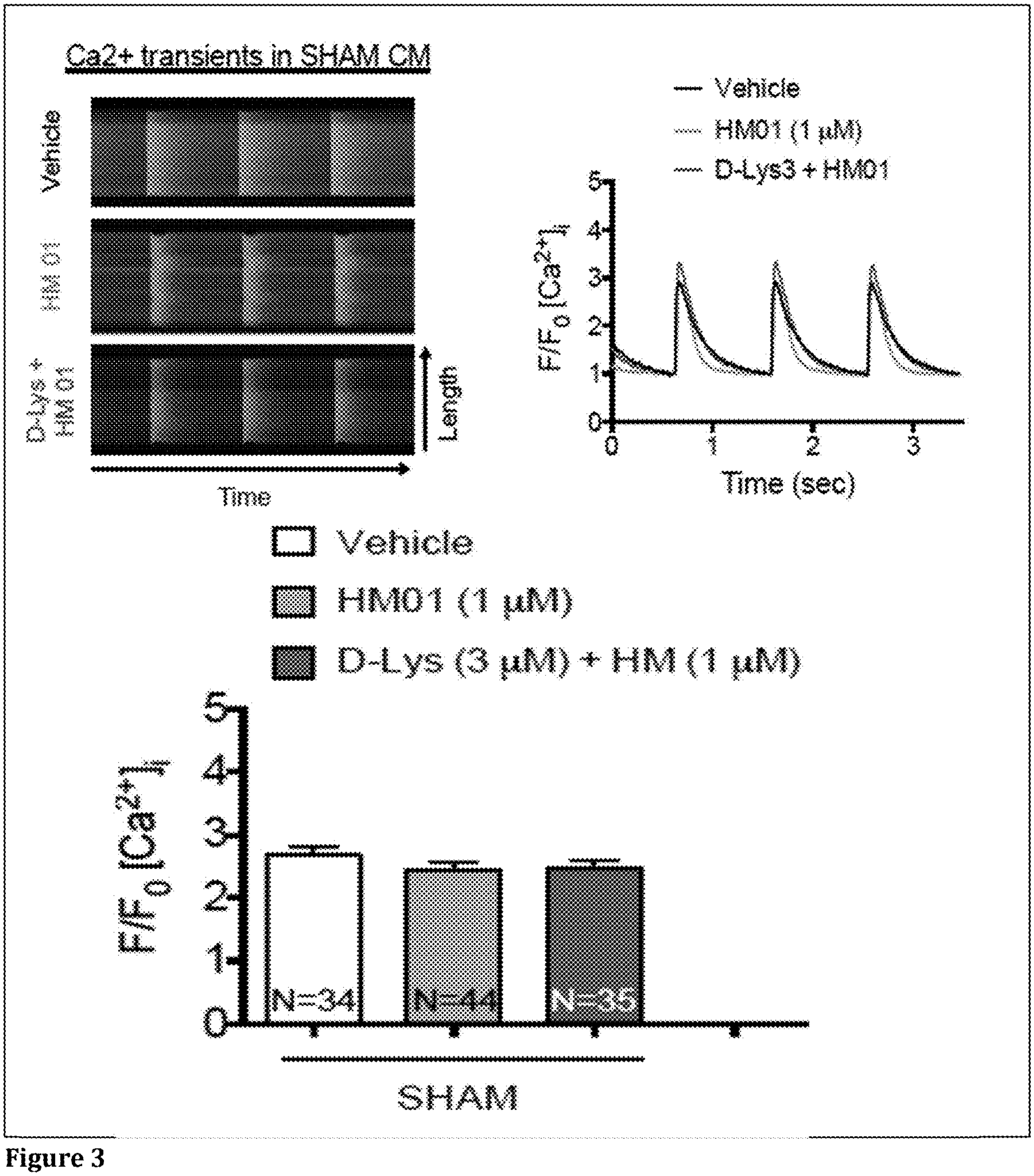
FIG. 3: Representative line scan and $Ca^{2+}$ transient curves in cardiomyocytes isolated from hearts of SHAM mice. Representative $Ca^{2+}$ transients line scan (left), representative amplitude changes curves (right) and average $Ca^{2+}$ transient amplitudes in cardiomyocytes isolated from hearts of SHAM mice (bottom). AC01/HM01 treatment (1 μM) with or without D-Lys 3 GHRP-6 did not change the $Ca^{2+}$ transient amplitude. Bar graphs show average of N cells analyzed as stated.

AC01/HM01 Increased Cardiomyocyte Contractility without Increasing $Ca^{2+}$ Transient Amplitudes (FIG. 2; FIG. 3)

All clinically available inotropes increase contractility by increasing intracellular $Ca^{2+}$ concentrations, which is responsible for their adverse safety profile. Therefore it was a surprise to observe that the increased contractility observed in FIG. 1 was achieved without altering $Ca^{2+}$ transients: FIG. 2 shows that no significant change in $Ca^{2+}$ transient amplitude was observed at any tested concentrations of AC01/HM01. Yet as seen in FIG. 1, AC01/HM01 increased fractional shortening (contractility). This suggests that the contractile effect is linked to enhanced $Ca^{2+}$ sensitivity rather than increased $Ca^{2+}$ release. FIG. 3 shows that AC01/HM01 did not increase $Ca^{2+}$ transients in SHAM cardiomyocytes. In cardiomyocytes from SHAM mice, AC01/HM01 with or without D-Lys3 pretreatment did not have any impact on $Ca^{2+}$ transient amplitudes compared to vehicle treated cells (FIG. 3). This further confirms that the contractile effect of AC01/HM01 is driven by an enhanced $Ca^{2+}$ sensitization mechanism, as in FIG. 2.

Figure 4:
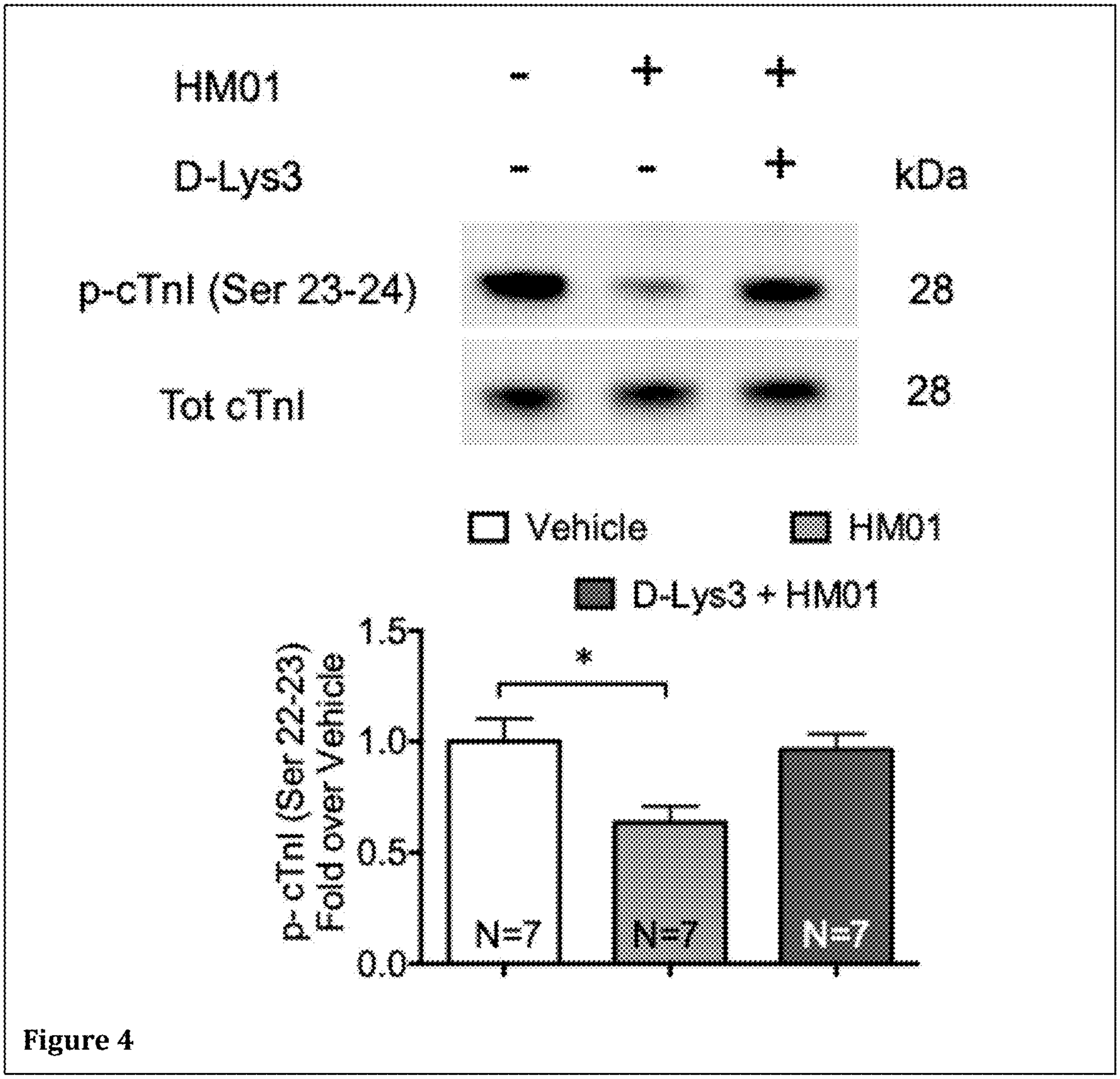
FIG. 4: Phospho (Ser 22-23) cTnl levels assessed by western blot. (top): Representative blot of phosphorylated cTnl and Total cTnl. Treatment of SHAM cardiomyocytes with AC01/HM01 (1 μM; middle column) reduced the levels of phosphorylation of cardiac Troponin I at residues Serine 22-23. Pretreatment with the ghrelin receptor antagonist, D-Lys3—GHRP-6 (3 μM, right column) blocked the signaling activated by AC01/HM01 in cardiomyocytes and restored the phosphorylation levels of cTnl to physiologic levels observed in vehicle treated cardiomyocytes (left column).

AC01/HM01 Reduced cTnl Phosphorylation which is Linked to Enhanced $Ca^{2+}$ Sensitivity (FIG. 4)

Changes in phosphorylation on serine residues 22-23 of the cardiac sarcomere protein cTnl have previously been shown to impact the myofilament $Ca^{2+}$ sensitivity in skinned mouse and rat myocytes through a cAMP-PKA dependent mechanism. In order to explore the molecular mechanism behind enhanced $Ca^{2+}$ sensitivity and contractility in our experimental model, SHAM mice cardiomyocyte suspension were treated with vehicle or AC01/HM01 with or without D-Lys 3, then processed for biochemistry analysis. FIG. 4 shows that in Western blot assays of protein extracts, cardiomyocytes treated with AC01/HM01 displayed decreased phosphorylation levels (middle column, grey bar) of cTnl (Serine 22-23) compared to vehicle treated cardiomyocytes (left column, white bar), while pretreatment with D-Lys3 blocked this effect (right column, red bar). These data are consistent with a model whereby AC01/HM01 activates the ghrelin receptor and increases the $Ca^{2+}$ sensitivity via reduction in cTnl phosphorylation.

Figure 5:
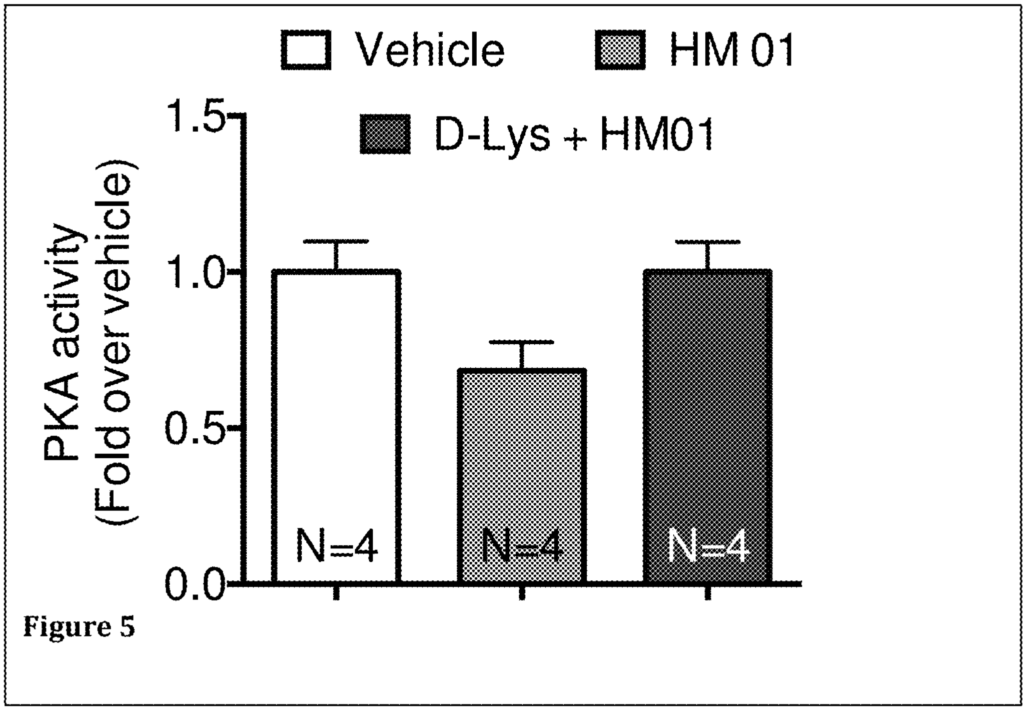

AC01/HM01 Reduced Cardiomyocyte PKA Activity and Reduced cTnl Phosphorylation (FIG. 5)

cTnl phosphorylation (Ser 22-23) is mediated by PKA. We therefore investigated if AC01/HM01 affected the enzyme activity of PKA. FIG. 5 shows that PKA activity decreased in cardiomyocytes treated with AC01/HM01 compared to vehicle and that this effect was blocked by pretreatment with D-Lys 3 prior to AC01/HM01 stimulation. This surprisingly suggests that the ghrelin receptor agonist AC01/HM01 may activate Ga inhibitory (Gai) signalling, which inhibits adenylate cyclase activity leading to reduced PKA activity.

DISCUSSION

Our data showed that AC01/HM01 but not vehicle increased cardiomyocyte contractility, in a dose dependent manner. To our surprise and in contrast to existing inotropes, AC01/HM01 increased contractility without increasing the cardiomyocyte $Ca^{2+}$ transient amplitudes suggesting that increased contractility occurred instead through increased myofilament $Ca^{2+}$ sensitivity.

The specific ghrelin antagonist, D-Lys 3 GHRP-6, blocked the effect of AC01/HM01 on cardiomyocyte contractility, which further confirms that the contractile effect is controlled by ghrelin receptor signalling. The AC01/HM01-induced increases in myofilament $Ca^{2+}$ sensitivity appears to be linked to ghrelin receptor G-α inhibitory (G-αi) signaling, which leads to reduction of PKA activity and a reduction in cTnl Ser 22-23 phosphorylation. This suggests a novel pharmacological way to influence myofilament function to increase contractility. These results highlight the potential use of this novel first in class molecule and novel mechanism of action for treatment of heart failure, increasing contractility and cardiac output without the mechanisms of conventional inotropes, which increase $Ca^{2+}$ concentrations and cause increased oxygen demand, tachycardia, arrhythmia, ischemia, and increased mortality.

Central to hemodynamic regulation is the autonomic nervous system that controls release of catecholamines (adrenaline and noradrenaline) from sympathetic nerve endings and the adrenal glands. An important function of this is regulation of the inotropic state in the heart. Activation of β-adrenergic receptors in the heart leads to stimulation of cAMP-PKA signaling, which results in an increased cardiac output due to increases heart rate (chronotropy), increases force of contraction (inotropy) and increased rate of relaxation (lusitropy). Increases cardiac force of contraction through cAMP-PKA activation depends on enhanced $Ca^{2+}$ signaling in the myocyte. An alternative mechanism to increase contractility, which does not require toxic potentiation of $Ca^{2+}$ release, is myofilament $Ca^{2+}$ sensitization. There is indeed a physiological mechanism for the regulation of the $Ca^{2+}$ sensitivity via PKA-dependent phosphorylation of cTnl at serine residues 22 and 23 (Ser22/23 in the mouse and Ser23/24 in human) at the N-terminal, which regulates the $Ca^{2+}$ binding affinity of cTnC. When cTnl is phosphorylated, myofilament $Ca^{2+}$ sensitivity is reduced and the force-$Ca^{2+}$ relationship curve becomes shifted rightwards (less force for a given $Ca^{2+}$ concentration). The evidence of inverse correlation between cTnl phosphorylation (Ser 22-23) and Ca2+ sensitivity of myofilaments finds an example in end-stage failing hearts that displayed reduced phosphorylation of cTnl and increased $Ca^{2+}$ sensitivity compared to donor hearts while treatment with PKA abolished any difference in $Ca^{2+}$ sensitivity between failing and non-failing myocytes. This suggests that in failing hearts there are compensatory mechanisms activated in order to improve contractility through enhanced $Ca^{2+}$ sensitivity. To our surprise, AC01/HM01 appeared to potentiate these $Ca^{2+}$ sensitivity mechanisms.

In summary, our data demonstrate that the novel molecule AC01/HM01 is a first in class new type of myotrope, that acts specifically on the ghrelin receptor and increases cardiomyocyte contractility. In contrast to conventional inotropes which act by deleterious increases in Ca2+ transients, AC01/HM01 instead reduces PKA activity and reduces cTnl phosphorylation, possibly through Gai mediated-receptor signalling and thus increases Ca2+ sensitivity (FIG. 6). This is the first report showing increased contractility of AC01/HM01 in cardiomyocytes. This study supports the use of AC01/HM01 as a treatment for reduced cardiac contractility in HF.

Example 2

In-Human, Single Ascending Dose, Phase 1, Randomized, Double-Blind, Placebo-Controlled Study to Assess the Safety and Pharmacokinetics of Orally Administered HMO1 in Male Healthy Volunteers Primary objectives To establish the maximum tolerated dose (MTD) through the assessment of the safety and tolerability of single ascending doses of oral HMO1 investigated up to a maximum dose of 10 mg.

To evaluate the pharmacokinetics (PK) of HMO1 and its metabolites (M2, M6 and M9) following single oral administration.

Secondary Objectives

To evaluate pharmacodynamics (PD) biomarkers.

To evaluate functional parameters related to the mechanism of action of HM01.

Study Design

Single-center, randomized, double-blind, placebo-controlled, single ascending dose (SAD) study.

Screening examinations were performed within 28 days prior to dosing. Eligible subjects returned to the study center in the morning of Day-1 and remained in-patient until discharge at 72 hours after dosing (morning of Day 4) if there were no safety issues. The oral dose was administered in the morning of Day 1. Subjects returned to the clinic 7 days after treatment, in the morning of Day 8 (±1 day), for the safety assessments.

After completion of all 72-hour assessments of a cohort, blinded safety and pseudonymized PK data were reviewed and the next dose increment was decided by the dose escalation committee (DEC).

Depending on the nature, frequency and severity of the safety profile, the DEC, including subject matter experts when opportune, decided whether to: • Continue with the dose escalation proceeding with the planned scheme; • Stop the dose escalation (i.e., no further dosing with study drug); • Continue with the dose escalation further to the planned doses, i.e., with doses>5 mg (but<10 mg).

Subjects Involved

Healthy male non-smoking subjects, between 18 and 50 years of age inclusive, with a body mass index (BMI) between 18.5 and 29.9 kg/$m^2$ inclusive. Cohorts of 8 subjects per dose step were planned. Cohort 1 (10 mg or placebo) was stopped after dosing of 4 subjects. Cohorts 2 to 4 consisted of 8 subjects each, i.e., a total number of 28 subjects were randomized and completed the study. There were no withdrawals.

Test Product, Dose and Mode of Administration

HM01 HCl powder in gelatine capsules. Capsules with the strength of 0.1 mg and 1.0 mg and 10 mg for cohort 1 were available.

Cohort 1:10 mg HM01

Cohort 2:0.1 mg HM01 Cohort 3:0.3 mg HM01 Cohort 4:1.0 mg HM01

The first cohort consisted of 4 subjects (3 active, 1 placebo).

Cohorts 2 to 4 consisted of 8 subjects, 6 subjects received a dose of HM01 and 2 subjects received placebo. For safety reasons each cohort was divided into 2 sub-groups: a first sub-group of 2 subjects (1 HM01, 1 placebo) and a second sub-group of 6 subjects (5 HM01, 1 placebo). The second sub-group was only started in absence of any major safety concerns as assessed by the Investigator following a minimum of at least 24 hours.

Subjects were dosed in a fasted state (no food for at least 8 hours). Access to food was restricted until 4 hours after dosing. Capsules were administered orally together with 240 mL water.

Safety Variables

Adverse events (AEs), vital signs (blood pressure, pulse rate and body temperature), 12-lead ECG, Holter-ECG, physical examination (PE), and laboratory tests (hematology, clinical chemistry, and urinalysis) assessed during screening and several times throughout the study.

Pharmacokinetic Variables

Blood samples for analytical assay of HM01 and the 3 major metabolites (M2, M6 and M9) were collected at pre-dose (within 60 minutes prior to drug administration), and at 0.25, 0.5, 1, 1.5, 2, 3, 4, 6, 8, 12, 16, 24, 30, 36, 48, 60 and 72 hours post dose (18 samples). Urine was collected for 24 hours after dosing. Blood and urine samples were analyzed for HM01 and its metabolites concentrations using validated LC-MS/MS methods.

PK parameters estimated included $C_{max}$ (maximum observed concentration), $C_{max}$/D ($C_{max}$ per dose unit), $t_{max}$ (peak time), Clast (last measurable concentration above the lower limit of quantification), $t_{last}$ (time of Clast), AUC(0-24) and $AUC_{last}$ (area under the plasma concentration-time curve from time zero to 24 hours and to the last measurable concentration, $t_{last}$, respectively), $AUC_{last}$/D ($AUC_{last}$ per dose unit), $AUC_{\infty}$(area under the plasma concentration-time curve from time zero to infinity), $AUC_{\infty}$(/D ($AUC_{\infty}$ per dose unit), $t_{1/2}$ (apparent terminal half-life), CL/F (systemic clearance after extravascular administration, only for the parent drug), Vz/F (apparent volume of distribution after extravascular administration, only for the parent drug), MRT (mean residence time).

Additional parameters were derived from urine, i.e., $Ae_{(0-24)}$, the amount of the parent drug and metabolites excreted in 24 h, and CLR, the renal clearance.

Pharmacodynamic Variables

Blood samples for determination of growth hormone (GH), insulin-like growth factor-1 (IGF-1), adrenocorticotropic hormone (ACTH), prolactin, cortisol and aldosterone in serum at pre-dose and 0.5, 1, 2, 3, 4, 6 and 24 hours post-dose were collected by venous puncture. All biomarkers were determined using enzyme linked immunosorbent assays (ELISA). Simplified nutritional appetite questionnaire based on appetite assessments at Day −1 after dinner, and on Day 1 pre-dose, 1, 2, 4, 8, and 24 hours after dosing. Stool diary starting on Day 1 until discharge on Day 4.

Results

Pharmacokinetics

A dose proportional increase in $AUC_{\infty}$ and max was observed for HM1 and M6. A slightly more than dose proportional increase was observed for $AUC_{last}$ for HM01 and M6 with slopes of 1.29 and 1.26, respectively, and 90% confidence intervals above 1. Arithmetic mean half-life (9 to 11 hours), median $t_{max}$ (3 to 4 hours), geometric mean clearance (55.9 to 65.8 L/h) and volume of distribution (801 to 911 L) of HM01 were similar for all doses. After administration of 0.1 mg to 10 mg HM01, arithmetic mean half-life of M6 ranged from 23 to 37 hours and median $t_{max}$ from 3.0 to 5.0 hours. The ratio of $AUC_{\infty}$ of M6 to HM01 was similar after administration of 0.3 and 1.0 mg HM01 (2.330, 2.336) and slightly lower for the 10 mg dose (1.761). Approximately 10% of the 10 mg dose was excreted in the urine as parent compound HM01 and 16% as M6.

Summary of the main PK parameters of HM01 (PK set)

| | 0.1 mg HM01 N = 6 | 0.3 mg HM01 N = 6 |
|---|---|---|
| $AUC_{0-24h}$ (h * ng/mL) | — | 3.747 (14.3) |
| $AUC_{last}$ (h * ng/mL) | 0.4899 (98.7) | 2.819 (39.8) |
| $AUC_{last}$/D (h * ng/mL)/mg | 4.899 (98.7) | 9.396 (39.8) |

-continued

| Summary of the main PK parameters of HM01 (PK set) | | |
|---|---|---|
| $AUC_\infty$ (h * ng/mL) | — | 4.558 (24.6)[a] |
| $AUC_\infty$/D (h * ng/mL)/mg | — | 15.19 (24.6)[a] |
| $C_{max}$ (ng/mL) | 0.1357 (20.9) | 0.2866 (26.7) |
| $C_{max}$/D (ng/mL)/mg | 1.357 (20.9) | 0.9554 (26.7) |
| $t_{max}$ (h) | 3.00 (2.0-3.0) | 4.00 (3.0-6.0) |
| $t_{last}$ (h) | 8.00 (4.0-8.0) | 16.00 (12.0-24.0) |
| $\lambda_z$ ($h^{-1}$) | — | 0.0821 (33.2)[a] |
| $t_{1/2}$ (h) | — | 8.830 (36.4)[a] |
| CL/F (L/h) | — | 65.8 (24.6)[a] |
| $V_z$/F (L) | — | 801.2 (12.5)[a] |
| MRT (h) | — | 14.45 (24.3)[a] |
| | 1.0 mg HM01 N = 6 | 10 mg HM01 N = 3 |
| $AUC_{0-24h}$ (h * ng/mL) | 13.42 (40.4) | 148.8 (32.3) |
| $AUC_{last}$ (h * ng/mL) | 14.71 (53.4) | 176.1 (37.7) |
| $AUC_{last}$/D (h * ng/mL)/mg | 14.71 (53.4) | 17.61 (37.7) |
| $AUC_\infty$ (h * ng/mL) | 16.94 (48.6) | 178.8 (37.1) |
| $AUC_\infty$/D (h * ng/mL)/mg | 16.94 (48.6) | 17.88 (37.1) |
| $C_{max}$ (ng/mL) | 1.280 (34.7) | 15.28 (47.1) |
| $C_{max}$/D (ng/mL)/mg | 1.280 (34.7) | 1.528 (47.1) |
| $t_{max}$ (h) | 4.00 (3.0-6.0) | 3.00 (2.0-3.0) |
| $t_{last}$ (h) | 36.00 (16.0-36.0) | 72.00 (48.0-72.0) |
| $\lambda_z$ ($h^{-1}$) | 0.0648 (27.7) | 0.0646 (19.8) |
| $t_{1/2}$ (h) | 11.00 (23.7) | 10.86 (18.6) |
| CL/F (L/h) | 59.0 (48.6) | 55.9 (37.1) |
| $V_z$/F (L) | 911.3 (28.1) | 865.6 (16.5) |
| MRT (h) | 15.33 (21.2) | 14.19 (11.4) |

Geometric mean and geometric CV (%) are presented except for $t_{1/2}$ where arithmetic mean and arithmetic CV (%) and for $t_{max}$ and $t_{last}$ where medians and ranges are given;
[a]n = 5 (due to unreliable determination of the terminal phase in one subject).

Pharmacodynamics

Concentrations of GH increased from baseline after HMO1 administration with peak concentrations at 2-3 hours post-dose. GH increase was higher after administration of 1.0 and 10 mg HM01, whereas lower increases were seen after 0.3 and 0.1 mg HM01.

Mean GH curves were similar after 1.0 and 10 mg HM01. After the peak, GH concentrations rapidly decreased. No relevant differences between the dose groups and placebo were observed for IGF-1 serum levels. Concentrations of ACTH, prolactin, cortisol and aldosterone rapidly increased above baseline values after administration of the higher doses of 1.0 and 10 mg HM01. Peak concentrations were generally observed at 2 to 3 hours post-dose. Thereafter, concentrations rapidly decreased. The increase was similar after 1.0 and 10 mg HMO1 except for prolactin, where the increase was higher after 10 mg compared to 1.0 mg, and ACTH, whose levels were determined only after the 1.0 mg HM01 dose. The appetite questionnaire showed no relevant or consistent differences between the dose groups and placebo. There were no dose-related differences between the dose groups for the number of bowel movements per day and the number of subjects with bowel movement.

Safety

The number of subjects reporting treatment emergent adverse events (TEAEs) and the number of TEAEs increased dose-dependently: no TEAEs were reported after 0.1 mg HM01, 2 subjects (33.3%) reported 5 TEAEs after 0.3 mg, 3 subjects (50.0%) reported 7 TEAEs after 1.0 mg and 3 subjects (100%) reported 19 TEAEs after 10 mg HMO1 compared to 5 subjects (71.4%) reporting 5 TEAEs after placebo.

Most frequently reported TEAEs were nervous system disorder (mainly headache) and cardiac disorders (mainly sinus bradycardia), which started mainly shortly after dosing and were of short duration. Most TEAEs were of mild intensity, TEAEs of moderate intensity were reported by 1 subject each after administration of 1.0 mg (hot flush) and 10 mg AC01 (sinus bradycardia) and placebo (headache). There were no clinically relevant differences between the dosing groups for any laboratory parameters. Mean systolic and diastolic blood pressure and body temperature showed no clinically relevant changes after dosing or differences between the treatment groups.

Example 3

Randomized, Double-Blind, Multiple Ascending Dose, Placebo-Controlled, Multi-Center, Safety, Tolerability, Efficacy, Pharmacokinetic (PK) and Pharmacodynamic (PD) Phase 1b/2a Trial with the Oral Ghrelin Agonist AC01 in Patients with Heart Failure with Reduced Ejection Fraction (HFrEF).

The study is focused on patients with HFrEF having reduced cardiac contractility, low cardiac output and maladaptive neurohormonal activation to maintain cardiac output, severe symptoms, and high rates hospitalization for worsening heart failure and death, and the above referred pre-clinical data suggesting that AC01 increases cardiomyocyte contractility through calcium sensitization rather than increasing calcium concentrations, and thus may improve cardiac contractility, cardiac output and clinical outcomes without the adverse effects of conventional inotropes.

Study Design

Multicenter, randomized, double-blind, placebo-controlled study conducted in 2 parts: a sequential cohort dose escalation phase (Part A) and a subsequent parallel cohort expansion phase (Part B). Patients will be randomized in a 3:1 ratio to receive AC01 or placebo minitablets BID in the fasted state for 7 days (dose escalation phase, Part A) or 28 days (cohort expansion phase, Part B).

Dose Escalation Phase (Part A)

Up to 40-56 patients equally divided in up to 7 cohorts. 6 active, 2 placebo patients per dose arm. Eight patients in each of initially 5 sequential dose cohorts will be treated BID with multiple ascending doses of AC01 (escalating from 0.1 mg twice daily, with up to 5 sequential dose levels) or placebo for 7 days. Up to 2 additional cohorts may be added if deemed necessary. Dose increments will not exceed 3.3-fold and will not be less than 25% higher than the dose level in the previous cohort. Dose escalation will stop upon reaching a total daily dose of 5 mg twice daily. Patients will have an ICD (to protect against ventricular arrythmia and severe bradycardia). Two dose levels will be selected, 1 for each group in the subsequent cohort expansion phase (Part B). Based on the outcome of the dose escalation phase (Part A), however, additional dose levels may be identified for the cohort expansion phase (Part B). The dose evaluation period will be from the first administration of AC01 up to Day 12 (5 days after last investigational medicinal product [IMP] administration in each cohort). There will be a minimum of 10 days between the Day 12 after the last IMP administration in 1 cohort and the first dose in the next cohort to allow adequate time for review of data by the Safety Review Committee (SRC)

Cohort Expansion Phase (Part B)

On completion of Part A, between 40 and 60 patients, different individuals from Part A, will be enrolled in Part B (cohort expansion). These patients will be divided into 2 dose cohorts and will be treated BID up to 28 days at the dose levels identified in Part A. If more than 2 dose levels are selected for the cohort expansion, the total number of patients per cohort and/or total number of cohorts will be reevaluated to cover all possible dose levels.

Investigational Product

AC01 is formulated as minitablets of 0.05 mg and 1 mg strength. Placebo is also delivered as minitablets of the same appearance, shape, smell, and taste of the AC01 tablets.

Objectives

Dose Escalation Phase (Part A)

Primary objective: To establish the safety and tolerability of multiple ascending doses of oral AC01 in ambulatory patients with stable HFrEF treated twice daily (BID) for 7 days and assess the recommended oses (RDs) for the cohort expansion phase (Part B)

Secondary objectives: To determine the PK of AC01; to determine the PD of AC01 and the PK/PD relationships.

Exploratory objective: To determine the effect of AC01 on clinical variables (direct effects, e.g., circulating GH; stroke volume [SV], and CO) related to its mode of action and target engagement and relevant for clinical outcomes in patients with stable HFrEF.

Cohort Expansion Phase (Part B)

Primary objective: To extend the assessment of safety and tolerability and perform exploratory assessment of efficacy in patients with stable HFrEF treated BID up to 28 days in two dose levels of AC01 emerging from the dose escalation phase (Part A). The exploratory efficacy of AC01 includes but is not limited to primary direct (circulating GH) and secondary direct and indirect hemodynamic and disease modifying effects (e.g., SV, CO, and other functional parameters such as echocardiographic indices and NT-proBNP)

Secondary objectives: to generate additional data on the PK of AC01; to generate additional data on the PD of AC01 and the PK/PD relationships.

The following safety outcomes (Parts A and B) are assessed:

Primary outcomes: Heart rate, systolic blood pressure, mean arterial blood pressure, physical exam (pulmonary, cardiac, extremities (edema)), arrhythmia (Holter electrocardiogram [ECG], 12-lead ECG, implantable cardioverter-defibrillator [ICD] reports, continuous telemetry), brady- or tachycardia (Holter ECG, 12-lead ECG, ICD reports, continuous telemetry [only Part A]), ischemia (symptoms, ECG changes, and/or hs-Troponin T/I), ECG intervals, i.e., heart rate, PR, QRS, and QTcF, plasma NT-proBNP, eGFR (potassium; sodium), Hematology (hemoglobin, white blood cell with differential, platelets), liver enzymes, adverse events (AEs), weight, plasma glucose.

Secondary outcomes: PK measures: For each cohort, PK parameters of AC01 and the potentially active M6 metabolite will be assessed to estimate rate and extent of the absorption, distribution, and elimination and support the interpretation of safety and efficacy findings. PD measures: PD will be assessed by safety measurements listed above and by exploratory efficacy measurements using biomarkers, noninvasive CO, echocardiography at time points in Schedule of Events.

The invention claimed is:

1. A method of treating a condition requiring inotropic treatment in a patient in need thereof, comprising administering said patient with a compound of formula (I)

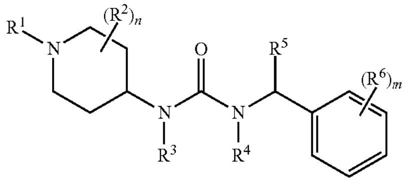

(I)

or a pharmaceutically acceptable salt thereof, wherein in formula (I):

each $R^2$, $R^3$, $R^5$, independently from each other are $C_1$-$C_6$ alkyl, $R^1$, $R^4$, independently from each other are hydrogen or $C_1$-$C_6$ alkyl, each $R^6$ independently from each other is $C_1$-$C_6$ alkyl, halo, $C_1$-$C_6$ alkoxy or $C_1$-$C_6$ haloalkyl, n is 2-3 m is 1-3.

2. The method according to claim 1, wherein said compound is free of side effects caused by increased calcium concentration.

3. The method according to claim 1, wherein $R^4$ is hydrogen.

4. The method according to claim 3, wherein n is 2.

5. The method according to claim 4, wherein $R^2$ is methyl.

6. The method according to claim 5, wherein the two $R^2$ groups are attached to the same carbon of the piperidine ring of formula (I).

7. The method according to claim 1, wherein one or more of the following conditions apply:

both $R^3$ and $R^5$ are $C_1$-$C_3$ alkyl;

m is 3;

each $R^6$ independently from each other is halo or alkoxy.

8. The method according to claim 1, wherein said compound of formula (I) is 1-[(1S)-1-(2,3-dichloro-4-methoxyphenyl)ethyl]-3-methyl-3-[(4R)-1-methyl-3,3-dimethyl-4-piperidyl]-urea.

9. The method according to claim 1, wherein said pharmaceutically acceptable salt is a monohydrochloride salt.

10. The method according to claim 1, wherein the condition is connected with a reduced and/or ineffective heart contractility in the patient in need thereof.

11. The method according to claim 1, wherein the condition is selected from heart failure, heart attack, cardiogenic shock, septic shock, myocardial infarction, cardiomyopathy, and pulmonary artery hypertension (PAH).

12. The method according to claim 11, wherein said cardiomyopathy is dilated cardiomyopathy (DCM).

13. The method according to claim 1 wherein the condition is severe, advanced, chronic or acute heart failure.

14. The method according to claim 1, wherein the condition is severe, advanced, chronic or acute heart failure with reduced heart ejection fraction.

15. The method according to claim 2, wherein said side effects due to increased calcium concentrations are selected from increased myocardial oxygen demand, ischemia, arrhythmia and hypotension.

16. The method according to claim 6, wherein the two $R^2$ groups are attached to the same carbon at the 3-yl position of the piperidine ring of formula (I).

17. The method according to claim 7, wherein one or more of the following conditions apply:

both $R^3$ and $R^5$ are methyl;

m is 3;

each $R^6$ independently from each other is halo or alkoxy and at least one $R^6$ is alkoxy.

18. The method according to claim 12, wherein said DCM is familial DCM.

* * * * *